(12) United States Patent
Rong et al.

(10) Patent No.: US 10,537,878 B2
(45) Date of Patent: Jan. 21, 2020

(54) CARBON-BASED MAGNESIUM-CONTAINING COMPOSITE MATERIAL AND SYNTHETIC METHOD THEREFOR

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Junfeng Rong, Beijing (CN); Chunfeng Shi, Beijing (CN); Jingxin Xie, Beijing (CN); Peng Yu, Beijing (CN); Mingsheng Zong, Beijing (CN); Weiguo Lin, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 97 days.

(21) Appl. No.: 15/546,821

(22) PCT Filed: Jan. 27, 2016

(86) PCT No.: PCT/CN2016/000060
§ 371 (c)(1),
(2) Date: Oct. 3, 2017

(87) PCT Pub. No.: WO2016/119569
PCT Pub. Date: Aug. 4, 2016

(65) Prior Publication Data
US 2018/0065107 A1    Mar. 8, 2018

(30) Foreign Application Priority Data

Jan. 27, 2015    (CN) .......................... 2015 1 0040939

(51) Int. Cl.
*B01J 21/18* (2006.01)
*B01J 27/10* (2006.01)
(Continued)

(52) U.S. Cl.
CPC ............. *B01J 21/185* (2013.01); *B01J 6/001* (2013.01); *B01J 21/10* (2013.01); *B01J 27/10* (2013.01);
(Continued)

(58) Field of Classification Search
None
See application file for complete search history.

(56) References Cited

U.S. PATENT DOCUMENTS

2005/0266990 A1* 12/2005 Iwasaki ................. H01G 11/34
                                                           502/416
2012/0322959 A1    12/2012 Masi et al.
2014/0335007 A1    11/2014 Katsoulis et al.

FOREIGN PATENT DOCUMENTS

CN            1814346 A        8/2006
CN         101415661 A         4/2009
(Continued)

OTHER PUBLICATIONS

Vercelli et al.; Magnesium Salts and Oxide: an XPS Overview; Applied Surface Science; 119, 253-259 (Year: 1997).*
(Continued)

*Primary Examiner* — Guinever S Gregorio
(74) *Attorney, Agent, or Firm* — Novick, Kim & Lee, PLLC; Allen Xue (57) ABSTRACT

A carbonaceous material, based on the total weight of the carbonaceous material, contains 1-99 wt % of a carbon
(Continued)

element, 0.2-60 wt % of a magnesium element, 0.5-60 wt % of an oxygen element and 0.1-40 wt % of a chlorine element. The process for preparing the carbonaceous material include (1) Mixing a solid carbon source, a precursor and water to produce a mixture; wherein said precursor contains a magnesium source and a chlorine source; (2) Drying the resulting mixture obtained in Step (1) to produce a dried mixture; and (3) Calcining the dried mixture obtained in Step (2). The carbonaceous material can be used in catalytic oxidation of hydrocarbons.

22 Claims, 2 Drawing Sheets

(51) Int. Cl.
| | | |
|---|---|---|
| B01J 6/00 | (2006.01) | |
| B01J 21/10 | (2006.01) | |
| B01J 37/02 | (2006.01) | |
| B01J 37/04 | (2006.01) | |
| B01J 37/08 | (2006.01) | |
| C07C 5/32 | (2006.01) | |

(52) U.S. Cl.
CPC ........... *B01J 37/0236* (2013.01); *B01J 37/04* (2013.01); *B01J 37/08* (2013.01); *C07C 5/324* (2013.01)

(56) References Cited

FOREIGN PATENT DOCUMENTS

| CN | 102731693 B | * | 9/2014 |
|---|---|---|---|
| CN | 102731693 B | | 9/2014 |

OTHER PUBLICATIONS

CN102731693 Google translation; Mar. 25, 2019.*
Vercelli et al.; Magnesium Salts and Oxide: an XPS Overview; Applied Surface Science; 119, 253-259; 1997.*
Zhijun Sui et al., "Microstructure of Carbon Nanofibers and Their Catalytic Performance for Oxidative Dehydrogenation of Propane", Chinese Journal of Catalysis, Jun. 2005, vol. 26, No. 6.

* cited by examiner

CARBON-BASED MAGNESIUM-CONTAINING COMPOSITE MATERIAL AND SYNTHETIC METHOD THEREFOR

TECHNICAL FIELD

The present invention relates to the field of material chemistry. Specifically, the present invention relates to a carbonaceous material, a process for preparing the carbonaceous material and use of said carbonaceous material.

BACKGROUND

The carbonaceous material comprises carbon nanotube, active carbon, graphite, graphene, fullerene, nano-carbon fiber and nano-adamas or the like. The carbonaceous material can be used as the catalytic material for oxidation of alkanes, for example, the active carbon can be used as a catalyst for oxidative dehydrogenation of ethylbenzene to produce styrene, and the active carbon can be used as a catalyst for conversion of n-butane to butene and butadiene.

The investigations show that the modification of the surface of the nano-carbon material (e.g. carbon nanotube and graphene) with a saturated and non-saturated functional group containing the heteroatoms such as oxygen and nitrogen can change the catalytic activity of the nano-carbon material. The nano-carbon material can be oxidized to introduce the oxygen atom into the nano-carbon material and increase the amount of the oxygen-containing functional groups in the nano-carbon material. For example, the nano-carbon material can be treated in a reflux condition of a strong acid (e.g. $HNO_3$, $H_2SO_4$) and/or a strong oxidative solution (e.g. $H_2O_2$, $KMnO_4$) optionally in the help of the microwave heating or the ultrasonic oscillation to enhance the oxidation effect.

However, the reflux treatment in the strong acid and/or the strong oxidative solution will have a negative effect on the framework structure of the nano-carbon material, and even destroy the framework structure of the nano-carbon material. For example, the oxidation of the nano-carbon material in a nitric acid solution can introduce a large amount of oxygen-containing functional groups to the surface of the nano-carbon material, but said treatment will be apt to cut off the nano-carbon material and/or remarkably increase the defect sites in the graphite network structure, and therefore reduce the properties of the nano-carbon material, e.g. thermostability. In addition, the amount of the oxygen atoms introduced by the reflux treatment in the strong acid and/or the strong oxidative solution has a high dependency on the reaction conditions, and will fluctuate widely, resulting in the difficulty of accurate control.

Olefins, especially diolefins and aromatic olefins, are important chemical feedstocks. For example, butadiene is a main raw material in production of synthetic rubbers such as styrene-butadiene rubber, butadiene rubber, nitrile rubber and chloroprene rubber. The copolymerization of styrene and butadiene to produce various widely used resins (e.g. ABS resin, SBS resin, BS resin and MBS resin) gradually plays an important role in production of resins. In addition, butadiene can also be used to produce ethylidene norbornene (a third monomer for ethylene propylene rubber), 1,4-butanediol, adiponitrile (nylon 66 monomer), sulfolane, anthraquinone and tetrahydrofuran, and butadiene is also an important basic chemical raw material. In addition, styrene is an important monomer in synthetic rubber and plastic, and can be used to produce styrene-butadiene rubber, polystyrene, polystyrene foam and the like. Styrene can be copolymerized with other monomers to produce engineering plastic for different uses, for example, styrene can be copolymerized with acrylonitrile and butadiene to produce ABS resin for use in a variety of household appliances and industry; with acrylonitrile to produce the SAN resin which is a resin having an impact resistance and a bright color and shade; and with butadiene to produce the SBS rubber, which is a thermoplastic rubber widely used as the modifier for polyvinyl chloride, polypropylene and the like. Styrene is mainly used in production of styrene resin and styrene butadiene rubber, but it is also one of raw materials in production of ion exchange resin and pharmaceutical. Moreover, styrene can be also used in pharmaceutical, dyes, pesticides and mineral processing industries.

Oxidative dehydrogenation is an important method for the production of olefins. For example, butane can be subjected to the oxidative dehydrogenation to produce 1-butene, which can be further subjected to the oxidative dehydrogenation to produce 1,3-butadiene; or phenylethane can be subjected to the oxidative dehydrogenation to produce styrene. However, the existing problem in the oxidative dehydrogenation to produce olefins is the difficulty in increasing both of the selectivity and the conversion, i.e., the difficulty in increasing the selectivity while increasing the conversion.

SUMMARY OF THE INVENTION

The object of the present invention is to solve the difficulty in increasing both of the selectivity and the conversion in the oxidative dehydrogenation to produce olefins. Therefore, the present invention provides a carbonaceous material capable of catalytic oxidative dehydrogenation to produce olefins with high selectivity and high conversion, a process for preparing said carbonaceous material, and use of said carbonaceous material.

The present inventors have surprisingly found that a carbonaceous material capable of catalytic oxidative dehydrogenation to produce olefins in a high selectivity and a high conversion can be formed by impregnating a catalytically active carbonaceous material with a precursor containing a magnesium source and a chlorine source followed by drying and calcining, wherein magnesium and chlorine can be very evenly integrated to the catalytically active carbonaceous material and magnesium can be very evenly distributed on the carbonaceous material, and therefore accomplished the present invention.

In an aspect, the present invention provides a carbonaceous material, based on the total weight of the carbonaceous material, the carbonaceous material contains 1-99 wt % of a carbon element, 0.2-60 wt % of a magnesium element, 0.5-60 wt % of an oxygen element and 0.1-40 wt % of a chlorine element; and in the XPS spectrum of the carbonaceous material, the binding energy characteristic peak of the 2 p electron of magnesium is located at >50.3 eV.

In another aspect, the present invention also provides a process for preparing a carbonaceous material, said process includes the following steps: (1) mixing a solid carbon source, a precursor and water to produce a mixture; wherein said precursor contains a magnesium source and a chlorine source; said magnesium source and said chlorine source are present in a dissolved state in the resulting mixture; the carbon element in said solid carbon source, and the magnesium element and the chlorine element in said precursor are present in a weight ratio of 1:(0.002-2):(0.01-20); (2) drying the resulting mixture obtained in Step (1) to produce a dried mixture; (3) calcining the dried mixture obtained in Step (2).

In another aspect, the present invention also provides a carbonaceous material prepared by the above process.

In yet another aspect, the present invention also provides use of the above carbonaceous material and the carbonaceous material prepared by the above process in the catalytic oxidation of hydrocarbons.

With the above technical solutions, the present invention can increase both of the selectivity and the conversion in oxidative dehydrogenation to produce olefins.

Specifically speaking, the present invention provides the following Solutions:

A1. A carbonaceous material, wherein based on the total weight of the carbonaceous material, the carbonaceous material contains 1-99 wt % of a carbon element, 0.2-60 wt % of a magnesium element, 0.5-60 wt % of an oxygen element and 0.1-40 wt % of a chlorine element; optionally but preferably in the XPS spectrum of said carbonaceous material, the binding energy characteristic peak of the 2 p electron of magnesium is located at >50.3 eV.

A2. The carbonaceous material according to any of previous Solutions, wherein based on the total weight of the carbonaceous material, the carbonaceous material contains 10-90 wt % of a carbon element, 2-50 wt % of a magnesium element, 2-50 wt % of an oxygen element and 1-30 wt % of a chlorine element.

A3. The carbonaceous material according to any of previous Solutions, wherein based on the total weight of the carbonaceous material, the carbonaceous material contains 20-80 wt % of a carbon element, 5-30 wt % of a magnesium element, 5-40 wt % of an oxygen element and 2-20 wt % of a chlorine element.

A4. The carbonaceous material according to any of previous Solutions, wherein based on the total weight of the carbonaceous material, the carbonaceous material contains 25-41 wt % of a carbon element, 20-30 wt % of a magnesium element, 19-40 wt % of an oxygen element and 4-20 wt % of a chlorine element.

A5. The carbonaceous material according to any of previous Solutions, wherein in the XPS of the carbonaceous material, the ratio of the content of the chlorine element as determined with the peak(s) in the range of 197.7-198.1 eV to the content of the chlorine element as determined with the peak(s) in the range of 199.7-200.1 eV is 0.5-2; the ratio of the content of the oxygen element as determined with the peak(s) in the range of 533.1-533.5 eV to the content of the oxygen element as determined with the peak(s) in the range of 531.8-532.2 eV is 0.2-5.

A6. The carbonaceous material according to any of previous Solutions, wherein in the different X-ray micro zones having the same area in the surface of the carbonaceous material, the coefficient of variation for the content of the Mg element is 20% or lower.

A7. The carbonaceous material according to any of previous Solutions, wherein said carbonaceous material has a peroxy group content of $\leq 2 \times 10^{-6}$ mol/g.

A8. The carbonaceous material according to any of previous Solutions, wherein said carbonaceous material has a peroxy group content of $\leq 1 \times 10^{-6}$ mol/g.

A9. The carbonaceous material according to any of previous Solutions, wherein said carbonaceous material has a peroxy group content of $\leq 0.8 \times 10^{-6}$ mol/g.

A10. The carbonaceous material according to any of previous Solutions, wherein the structural form of said carbonaceous material comprises at least one structural form selected from carbon nanotube, graphene, fullerene, nano-carbon particle, active carbon, thin-layer graphite, nano-carbon fiber and nano-adamas.

A11. A process for preparing a carbonaceous material, wherein said process includes the following steps:

(1) Mixing a solid carbon source, a precursor and water to produce a mixture; wherein the precursor contains a magnesium source and a chlorine source, said magnesium source and said chlorine source are present in a dissolved state in the resulting mixture; the carbon element in said solid carbon source, and the magnesium element and the chlorine element in said precursor are present in a weight ratio of 1:(0.002-2):(0.01-20);

(2) Drying the resulting mixture obtained in Step (1) to produce a dried mixture;

(3) Calcining the dried mixture obtained in Step (2).

A12. The process according to Solution A11, wherein, the carbon element in said solid carbon source, and the magnesium element and the chlorine element in said precursor are present in a weight ratio of 1:(0.01-1):(0.1-10).

A13. The process according to any of Solutions A11-A12, wherein the weight ratio of water to the solid carbon source is (0.1-200):1.

A14. The process according to any of Solutions A11-A13, wherein the calcination temperature is 200-500° C., the calcination time is 0.5-48 hours.

A15. The process according to any of Solutions A11-A14, wherein the calcination temperature is 300-450° C.

A16. The process according to any of Solutions A11-A15, wherein the calcination is conducted in an oxygen-containing gas, based on the total volume of the oxygen-containing gas, the oxygen-containing gas has an oxygen content of 2-25 vol %.

A17. The process according to any of Solutions A11-A16, wherein said solid carbon source includes at least one of carbon nanotube, graphene, fullerene, nano-carbon particle, thin-layer graphite, active carbon, nano-carbon fiber and nano-adamas; said magnesium source includes at least one of magnesium nitrate, magnesium nitrite, magnesium oxalate, magnesium oxide, magnesium hydroxide, magnesium sulfate, magnesium sulfite, magnesium tartrate, magnesium sulfide, magnesium cyanide, magnesium thiosulfate, magnesium rhodanate, magnesium iodide, magnesium chloride, magnesium bromide, magnesium acetate and magnesium carbonate; said chlorine source includes at least one of chlorine gas, magnesium chloride, hydrogen chloride, hypochlorous acid, magnesium hypochlorite, chloric acid, magnesium chlorite, perchloric acid and magnesium perchlorite.

A18. The process according to any of Solutions A11-A17, wherein said precursor contains magnesium chloride and/or magnesium nitrate.

A19. A carbonaceous material obtained with the process according to any of Solutions A11-A18.

A20. Use of the carbonaceous material according to any of previous Solutions in the catalytic oxidation of hydrocarbons.

A21. Use according to Solution A20, wherein said hydrocarbon has a carbon atom number of 2-15, said hydrocarbon comprises at least one of an alkane, an alkene and an aromatic hydrocarbon containing alkyl group(s); said alkyl contains at least two carbon atoms.

A22. Use according to Solution A20, wherein said hydrocarbon comprises at least one of butane, 1-butene, ethylbenzene, propane, ethane and pentane.

The present invention also provides the following Solutions:

B1. A carbonaceous material, wherein based on the total weight of the carbonaceous material, the carbonaceous material contains 1-99 wt % of carbon, 0.2-60 wt % of magnesium, 0.5-60 wt % of oxygen and 0.1-40 wt % of chlorine; and in the XPS spectrum of the carbonaceous material, the binding energy characteristic peak of the 2 p electron of magnesium is located at >50.3 eV.

B2. The carbonaceous material according to Solution B1, wherein based on the total weight of the carbonaceous material, the carbonaceous material contains 10-90 wt % of carbon, 2-50 wt % of magnesium, 2-50 wt % of oxygen and 1-30 wt % of chlorine.

B3. The carbonaceous material according to Solution B2, wherein based on the total weight of the carbonaceous material, the carbonaceous material contains 20-80 wt % of carbon, 5-30 wt % of magnesium, 5-40 wt % of oxygen and 2-20 wt % of chlorine.

B4. The carbonaceous material according to any of Solutions B1-B3, wherein in the different X-ray micro zones having the same area in the surface of the carbonaceous material, the coefficient of variation for the content of the Mg element is 20% or lower.

B5. The carbonaceous material according to any of Solutions B1-B3, wherein said carbonaceous material comprises at least one structure selected from carbon nanotube, graphene, fullerene, nano-carbon particle, active carbon, nano-carbon fiber and nano-adamas.

B6. A process for preparing a carbonaceous material, wherein said process includes the following steps:

(1) Mixing a solid carbon source, a precursor and water to produce a mixture; wherein the precursor contains a magnesium source and a chlorine source, said magnesium source and said chlorine source are present in a dissolved state in the resulting mixture; the carbon element in said solid carbon source, and the magnesium element and the chlorine element in said precursor are present in a weight ratio of 1:(0.002-2):(0.01-20);

(2) Drying the resulting mixture obtained in Step (1) to produce a dried mixture;

(3) Calcining the dried mixture obtained in Step (2).

B7. The process according to Solution B6, wherein the carbon element in said solid carbon source, and the magnesium element and the chlorine element in said precursor are present in a weight ratio of 1:(0.01-1):(0.1-10).

B8. The process according to Solution B6 or B7, wherein the weight ratio of water to the solid carbon source is (0.1-200):1.

B9. The process according to Solution B6 or B7, wherein the drying temperature is 60-250° C., the time is 0.5-24 hours.

B10. The process according to Solution B6, wherein the calcination is conducted in an oxygen-containing gas, based on the total volume of the oxygen-containing gas, the oxygen-containing gas has an oxygen content of 0.5-25 vol %.

B11. The process according to Solution B6 or B10, wherein the calcination temperature is 200-500° C., the calcination time is 2-12 hours.

B12. The process according to Solution B6, wherein said solid carbon source comprises at least one of carbon nanotube, graphene, fullerene, active carbon, nano-carbon fiber and nano-adamas.

B13. The process according to Solution B6, wherein said precursor contains magnesium chloride and/or magnesium nitrate.

B14. The carbonaceous material prepared by the process according to any of Solutions B6-B13.

B15. Use of the carbonaceous material according to any of Solutions B1-5 and B14 in oxidative dehydrogenation of hydrocarbons.

B16. Use according to Solution B15, wherein said hydrocarbon has a carbon atom number of 2-12, said hydrocarbon comprises at least one of an alkane, an alkene and an aromatic hydrocarbon containing alkyl group(s).

B17. Use according to Solution B16, wherein said hydrocarbon comprises at least one of butane, 1-butene, ethylbenzene, propane, ethane and pentane.

The present invention also provides the following Solutions:

C1. A carbonaceous material, wherein based on the total weight of the carbonaceous material, the carbonaceous material contains 1-99 wt % of a carbon element, 0.2-40 wt % of a magnesium element, 5-30 wt % of an oxygen element and 0.1-30 wt % of Group VIIA element; and the carbonaceous material has a peroxy group content of $\leq 2\times 10^{-6}$ mol/g.

C2. The carbonaceous material according to Solution C2, wherein based on the total weight of the carbonaceous material, the carbonaceous material contains 10-90 wt %, 40-80 wt %, 50-80 wt % or 60-75 wt % of a carbon element.

C3. The carbonaceous material according to any of Solutions C1-C2, wherein based on the total weight of the carbonaceous material, the carbonaceous material contains 2-35 wt %, 5-30 wt %, 5-20 wt %, 5-15 wt % or 6-12 wt % of a magnesium element.

C4. The carbonaceous material according to any of Solutions C1-C3, wherein the carbonaceous material contains 5-30 wt %, 5-25 wt %, 8-25 wt % or 10-20 wt % of an oxygen element.

C5. The carbonaceous material according to any of Solutions C1-C4, wherein the carbonaceous material contains 1-25 wt %, 2-20 wt %, 2-15 wt % or 5-15 wt % of Group VIIA element; said Group VIIA element can be one or more of F, Cl, Br and I; said Group VIIA element preferably is Cl.

C6. The carbonaceous material according to any of Solutions C1-05, wherein the carbonaceous material has a peroxy group content of $\leq 1\times 10^{-6}$ mol/g; preferably, the carbonaceous material has a peroxy group content of $\leq 0.5\times 10^{-6}$ mol/g or $0.2\text{-}2\times 10^{-6}$ mol/g.

C7. The carbonaceous material according to any of Solutions C1-C6, wherein the carbonaceous material comprises at least one structure selected from carbon nanotube, fullerene, nano-carbon particle, active carbon, nano-carbon fiber and nano-adamas.

C8. The carbonaceous material according to any of Solutions C1-C7, wherein, in the XPS spectrum of said carbonaceous material, the binding energy characteristic peak of the 2 p electron of magnesium is located at >50.3 eV.

C9. A process for preparing a carbonaceous material, wherein said process includes the following steps: (1) contacting the starting carbonaceous material with a Grignard reagent in an inactive atmosphere; (2) removing the unreacted Grignard reagent with a solvent; (3) drying the carbonaceous material obtained from Step (2).

C10. The process according to Solution C9, wherein in Step (1), the mole ratio of the Grignard reagent to the oxygen of the starting carbonaceous material is 0.01-10, preferably 0.1-5.

C11. The process according to any of Solutions C9-C10, wherein in Step (1), said carbonaceous material is contacted with the Grignard reagent, the contacting temperature is 0-200° C., and the contacting time is at least one hour, preferably 2-100 hours, 2-28 hours or 2-24 hours.

C12. The process according to any of Solutions C9-C11, wherein said Grignard reagent is at least one compound having a formula of RMgX, wherein R is an aromatic group or an alkyl, X is a halogen element, preferably F, Cl or Br; the starting carbonaceous material is one or more of an oxygen-containing carbon nanotube, an oxygen-containing fullerene, an oxygen-containing nano-carbon particle, an oxygen-containing active carbon, an oxygen-containing nano-carbon fiber and an oxygen-containing nano-adamas.

C13. The process according to any of Solutions C9-C12, wherein said inactive atmosphere is one or more of nitrogen, argon, and helium.

C14. The process according to any of Solutions C9-C13, wherein the starting carbonaceous material has an oxygen content of 5-40 wt %, preferably 5-35 wt %, 5-30 wt %, 5-25 wt % or 5-20 wt %.

C15. The process according to any of Solutions C9-C14, wherein the starting carbonaceous material is obtained through oxidation by calcining an oxygen-free carbonaceous material and/or a low-oxygen-content carbonaceous material in an oxygen-containing atmosphere and/or by contacting with an oxidative strong acid, wherein said oxidation increases the oxygen content of the oxygen-free carbonaceous material and/or the low-oxygen-content carbonaceous material, wherein the oxygen content after the oxidation is at least 0.1 wt % higher than the oxygen content before the oxidation.

C16. The process according to any of Solutions C9-C15, wherein in Step (1), said contacting is conducted in the presence of a solvent, the weight ratio of said solvent to the starting carbonaceous material is preferably ≤30:1, e.g. 7-30:1 or 10-20:1.

C17. The process according to any of Solutions C9-C16, wherein in Step (1) or (2), said solvent is an ether and/or tetrahydrofuran; said ether is preferably one or more of ethers having 2-8 carbon atoms in the molecule, said solvent is preferably diethylether and/or tetrahydrofuran.

C18. The process according to any of Solutions C9-C17, wherein the starting carbonaceous material has a peroxy group content of $\geq 0.5\times 10^{-6}$ mol/g, for example, $\geq 2\times 10^{-6}$ mol/g.

C19. Use of said carbonaceous material according to any of Solutions C1-C8 in the catalytic oxidation of hydrocarbons.

C20. Use according to Solution C19, wherein said hydrocarbon has a carbon atom number of 2-15, said hydrocarbon comprises at least one of an alkane, an alkene and an aromatic hydrocarbon containing alkyl group(s); said hydrocarbon is preferably one or more of butane, 1-butene, ethylbenzene, propane, ethane and pentane.

Other characteristics and advantages of the present invention will be discussed in the following detailed description.

BRIEF DESCRIPTION OF THE DRAWING

The drawings are provided for the better understanding of the present invention and constitute a part of the specification. The drawings are provided for explaining the present invention together with the following detailed description, but have no limitation to the present invention in any way.

DETAILED DESCRIPTION

The specific embodiments of the present invention will be described in details hereinafter. It should be understood that the specific embodiments described herein is for the purpose of explaining the present invention rather than limiting the present invention in any way.

The present invention provides a carbonaceous material, based on the total weight of the carbonaceous material, the carbonaceous material contains 1-99 wt % of a carbon element, 0.2-60 wt % of a magnesium element, 0.5-60 wt % of an oxygen element and 0.1-40 wt % of a chlorine element, and in the XPS spectrum of the carbonaceous material, the binding energy characteristic peak of the 2 p electron of magnesium is located at >50.3 eV.

In the present invention, unless indicated to the contrary, the volume values for gas and liquid are those measured at 20° C. under 1 atm.

In the present invention, the elemental contents of the carbonaceous material are those measured by drying the carbonaceous material at 300° C. in a helium atmosphere for 3 hours, followed by using the X-ray fluorescence (XRF) elemental analysis. The XRF elemental analysis is well known in the art and will not be detailed herein.

In the present invention, the X-ray photoelectron spectroscopy is shortened as XPS. The XPS spectrum can be obtained with a conventional instrumental analysis method. The amount of the element as determined with the peak(s) in the specific range in the XPS can be calculated according to a conventional calculation method in the instrumental analysis field. For example, the measurement can be conducted according to the specifications accompanied with the specific X-ray photoelectron spectroscoper and the quantitative calculation can be done with the data treatment software shipped with the X-ray photoelectron spectroscoper. The present invention has no particular requirement in the XPS analysis.

In the present invention, from the viewpoint of further improving the catalytic capability of said carbonaceous material, preferably, based on the total weight of the carbonaceous material, the carbonaceous material contains 10-90 wt % of a carbon element, 2-50 wt % of a magnesium element, 2-50 wt % of an oxygen element and 1-30 wt % of a chlorine element; more preferably, based on the total weight of the carbonaceous material, the carbonaceous material contains 20-80 wt % of a carbon element, 5-30 wt % of a magnesium element, 5-40 wt % of an oxygen element and 2-20 wt % of a chlorine element; further preferably, based on the total weight of the carbonaceous material, the carbonaceous material contains 25-41 wt % of a carbon element, 20-30 wt % of a magnesium element, 19-40 wt % of an oxygen element and 4-20 wt % of a chlorine element. In a preferable embodiment of the present invention, said carbonaceous material substantially consists of a carbon element, a magnesium element, an oxygen element and a chlorine element, wherein the term "substantially consists of" means the carbon element, the magnesium element, the oxygen element and the chlorine element comprise 90 wt % or higher, e.g. 95 wt % or higher, 98 wt % or higher, preferably 99 wt % or higher of said carbonaceous material.

The present invention also provides a carbonaceous material, which contains a carbon element and modification elements of oxygen, magnesium and halogen, the content of the carbon element is 1-99 wt %, e.g. 10-90 wt %, 20-85 wt %, 40-80 wt %, 40-75 wt %, 50-80 wt %, 55-80 wt % or 60-75 wt %; the content of the oxygen element is 5-30 wt %, e.g. 5-25 wt %, 8-25 wt %, 5-20 wt %, 10-25 wt % or 10-20 wt %; the content of the magnesium element is 0.2-40 wt %, e.g. 1-35 wt %, 2-35 wt %, 5-30 wt %, 5-25 wt %, 3-20 wt %, 5-15 wt % or 6-12 wt %, the content of halogen is 0.1-30 wt %, e.g. 1-25 wt %, 2-20 wt %, 2-15 wt %, 6-15 wt % or 5-15 wt %. Said halogen is one or more of F, Cl, Br and I, preferably Cl. In an embodiment, the carbonaceous material of the present invention can also contain a hydrogen element. The content of the hydrogen element is ≤5 wt %, e.g. 0-5 wt %, 0.1-4.5 wt %, 0.3-4 wt %, 0.5-3.5 wt % or 0.5-3 wt % or 0.7-2.5 wt %. The carbonaceous material of the present invention can further contain other elements besides C, H, O, Mg and Group VIIA elements. The content of said other elements can be 0-98 wt %, e.g. 0-85 wt % or 0-48 wt %, 0.2-30 wt %. Said other elements can be for example, one or more of Group IA elements except H, Group IIA elements except Mg, Group IIIA elements, Group IVA elements except C, Group VA elements, Group VIA elements except O, and transition metal elements. For example, said other element can be one or more of sulfur element, silicon element, aluminium element, transition metal elements, nitrogen element, iron element, sulfur element, and phosphorus element.

According to the carbonaceous material of the present invention, preferably, in its XPS spectrum, the binding energy characteristic peak of the 2 p electron of magnesium is located at >50.3 eV, e.g. 50.4-52.0 eV or 50.6-51.4 eV.

The carbonaceous material can also have the following structural characteristics: in the XPS of the carbonaceous material, which is obtained after being placed at 300° C. in a helium atmosphere for 3 hours, the ratio of the content of the chlorine element as determined with the peak(s) in the range of 197.7-198.1 eV to the content of the chlorine element as determined with the peak(s) in the range of 199.7-200.1 eV is 0.5-2; in the XPS of the carbonaceous material, which is obtained after being placed at 300° C. in a helium atmosphere for 3 hours, the ratio of the content of the oxygen element as determined with the peak(s) in the range of 533.1-533.5 eV to the content of the oxygen element as determined with the peak(s) in the range of 531.8-532.2 eV is 0.2-5.

According to the carbonaceous material of the present invention, preferably, the magnesium element is distributed evenly. As determined with the X-ray micro zone elemental analysis, in the different X-ray micro zones having the same area in the surface of the carbonaceous material, the coefficient of variation for the content of the Mg element is 20% or lower, more preferably 15% or lower, particularly preferably 10% or lower, more particularly preferably 5% or lower. The X-ray micro zone refers to the observation zones selected for the X-ray micro zone elemental analysis. The concept "coefficient of variation" refers to the present of the standard deviation of multiple measurement values relative to the mean number of said multiple measurement values, i.e., the coefficient of variation (CV)=(standard deviation SD/mean number MN)×100%. The X-ray micro zone elemental analysis can be done according to a conventional instrumental analysis method. For example, the measurement method for the carbon nanotube can be as follows: the carbon nanotube having a length in a range of 25-250 nm is scanned with an energy spectrum analysis instrument in the length direction to determine the concentration or content of the magnesium atoms in said length direction (wherein five concentration or content values are measured). Five samples prepared from the same nano-carbon material are subjected to the scanning electron microscope-energy spectrum analysis, and five different carbon nanotubes for each sample are scanned. 25 concentration or content values of the magnesium atom are obtained and the corresponding coefficient of variation for the concentration or content of the magnesium atoms can be calculated. In this example, the coefficient of variation is a percent of the standard deviation of 25 measurement values relative to the mean number of said 25 measurement values, i.e. the coefficient of variation CV= (standard deviation SD/mean number MN)×100%. In order to reflect the distribution uniformity of the magnesium element in the carbonaceous material, the selected surface area of the carbonaceous material in the X-ray micro zone elemental analysis can be 10-250 $nm^2$, preferably 20-200 $nm^2$.

According to the carbonaceous material of the present invention, said carbonaceous material can have a peroxy group content of $\leq 2\times 10^{-6}$ mol/g, preferably $\leq 1\times 10^{-6}$ mol/g. According to the carbonaceous material of the present invention, said carbonaceous material has a peroxy group content of $\geq 0.01\times 10^{-6}$ mol/g, e.g. $\geq 0.1\times 10^{-6}$ mol/g or $\geq 0.2\times 10^{-6}$ mol/g. In an embodiment, said carbonaceous material can have a peroxy group content of $0.2\times 10^{-6}$ mol/g to $2\times 10^{-6}$ mol/g. In an embodiment, said carbonaceous material has a peroxy group content of $\leq 0.8\times 10^{-6}$ mol/g. In another embodiment, said carbonaceous material has a peroxy group content of $\leq 0.5\times 10^{-6}$ mol/g.

In the present invention, the peroxy group of said carbonaceous material can be measured by the iodometric method which is well known to those skilled in the art, for example, those discussed in F. P. Greenspan, D. G. Mackellar: *Analytical Chemistry*, 1948, 20, 1061-1063.

The structural form of said carbonaceous material comprises at least one structural form selected from carbon nanotube, graphene, fullerene, nano-carbon particle, active carbon, thin-layer graphite, nano-carbon fiber and nano-adamas.

Said carbonaceous material can be a mixture of carbonaceous materials selected from carbon nanotube, graphene, fullerene, nano-carbon particle, active carbon, thin-layer graphite, nano-carbon fiber and nano-adamas. Said carbonaceous material can also be selected from carbon nanotube, graphene, fullerene, nano-carbon particle, active carbon, thin-layer graphite, nano-carbon fiber and nano-adamas.

In an embodiment of the carbonaceous material according to the present invention, based on the total weight of the carbonaceous material, the carbonaceous material contains 1-99 wt % of a carbon element, 0.2-40 wt % of a magnesium element, 5-30 wt % of an oxygen element and 0.1-30 wt % of a halogen element (Group VIIA elements); and the carbonaceous material has a peroxy group content of $\leq 2\times 10^{-6}$ mol/g; preferably, based on the total weight of the carbonaceous material, the carbonaceous material of the present invention contains 10-90 wt % of a carbon element, 2-35 wt % of a magnesium element, 5-30 wt % of an oxygen element and 1-25 wt % of a halogen element, preferably a chlorine element; the content of the peroxy group of said material is preferably $\leq 1\times 10^{-6}$ mol/g, more preferably $\leq 0.5\times 10^{-6}$ mol/g; more preferably, based on the total weight of the carbonaceous material, the carbonaceous material of the present invention contains 50-80 wt % of a carbon element, 5-30 wt % of a magnesium element, 5-25 wt % of an oxygen element and 2-15 wt % of a halogen element, preferably a chlorine element; the content of the peroxy group of said material is preferably $\leq 0.5\times 10^{-6}$ mol/g.

In an embodiment of the carbonaceous material according to the present invention, the carbonaceous material contains 60-75 wt % of a carbon element, 5-15 wt % of a magnesium element, 10-25 wt % of an oxygen element and 6-15 wt % of Group VIIA element.

In an embodiment of the carbonaceous material according to the present invention, the carbonaceous material comprises at least one of carbon nanotube, fullerene, nano-carbon particle, active carbon, nano-carbon fiber and nano-adamas.

The carbonaceous material of the present invention is an oxygen-containing carbonaceous material having a relatively low content of the peroxy group (—O—O—). The carbonaceous material of the present invention can be used as catalyst in the oxidative dehydrogenation of hydrocarbons, and have a relatively high catalytic capability for the oxidation of hydrocarbons. For the oxidative dehydrogenation of hydrocarbons, both of the conversion of the starting hydrocarbon material and the selectivity for the target products are high. The preparation process for the carbonaceous material of the present invention can produce such a carbonaceous material that has relatively high oxygen content and relatively low peroxy content, and therefore improve the carbonaceous material in the aspect of conversion and selectivity properties. Use of the carbonaceous material of the present invention can enhance the conversion and the selectivity for the oxidative dehydrogenation to produce olefins.

Preparation Process 1

The present invention also provides a process for preparing a carbonaceous material, said process includes the following steps: (1) Mixing a solid carbon source, a precursor and water to produce a mixture; wherein said precursor contains a magnesium source and a chlorine source; said magnesium source and said chlorine source are present in a dissolved state in the resulting mixture; the carbon element in said solid carbon source, and the magnesium element and the chlorine element in said precursor are present in a weight ratio of 1:(0.002-2):(0.01-20); (2) Drying the resulting mixture obtained in Step (1) to produce a dried mixture; (3) Calcining the dried mixture obtained in Step (2).

According to the process of the present invention, the weight ratio of the carbon element in said solid carbon source to the magnesium element and the chlorine element in said precursor can be selected in a wide range, for example, 1:(0.002-2):(0.01-20), preferably 1:(0.01-1):(0.1-10), more preferably 1:(0.5-1):(0.1-1.48).

According to the process of the present invention, the weight ratio of water to said solid carbon source can be selected in a wide range, for example, (0.1-200):1, e.g. (1-100):1, more preferably (2-80):1, more preferably (3-50):1, further preferably (40-50):1.

According to the process of the present invention, the magnesium source and the chlorine source in said precursor are selected so that the magnesium element and the chlorine element in the mixture obtained in Step (1) are present in a dissolved state. For example, in case that said magnesium source contains magnesium oxide, said chlorine source can contain hydrochloric acid, so that the magnesium element and the chlorine element in the mixture obtained in Step (1) are present in a dissolved state.

According to the process of the present invention, in Step (1), the temperature and the time of the mixing can be selected in a wide range, for example, the time of the mixing can be 0.5-72 h, and the temperature of the mixing can be 20-80° C.

According to the process of the present invention, the purpose of the drying is to remove water used in the impregnation, which is favorable for the calcination. The drying conditions can be selected in a wide range, and is not particularly limited in the present invention. The drying conditions can be conventionally selected. Preferably, the drying temperature is 60-180° C., and the time is 0.5-24 hours. Said drying can be done at a normal pressure or a reduced pressure.

According to the process of the present invention, said calcination can be conducted in an inactive atmosphere, or in an oxygen-containing atmosphere, or successively in an inactive atmosphere and in an oxygen-containing atmosphere. Said inactive atmosphere refers to an atmosphere formed from at least one inactive gas, wherein said inactive gas is for example a gas of Group 18 (e.g. argon) and/or nitrogen. Preferably, said calcination is conducted in an oxygen-containing gas, based on the total volume of the oxygen-containing gas, the oxygen-containing gas has an oxygen content of 0.5-25 vol %. More preferably, said calcination is conducted in air.

The calcination condition can be selected in a wide range. For example, the calcination temperature is 200-500° C., preferably 300-450° C., the calcination time is 0.5-48 h, preferably 2-24 h. The heating procedure in the calcination can follow a programmed temperature rising strategy, for example, the calcination is firstly conducted at 200-300° C. for 1-12 hours, and then at a temperature of >300-450° C., e.g. 320-450° C. for 1-12 hours. The calcination can be followed by a natural cooling to room temperature. The calcination at a preferable range of 300-450° C. can further improve both of the selectivity and the conversion in the oxidation to produce olefins.

Said solid carbon source can be those conventionally used in the carbon catalysis field as long as said solid carbon source have a catalytic function for catalytic oxidation of hydrocarbons. For example, said solid carbon source can comprise at least one of carbon nanotube, graphene, fullerene, nano-carbon particle, active carbon, thin-layer graphite, nano-carbon fiber and nano-adamas. Preferably, said solid carbon source comprises at least one of carbon nanotube, nano-adamas and graphene.

Said carbon nanotube can comprise a single-walled carbon nanotube and/or a multi-walled carbon nanotube. The specific surface area of Said carbon nanotube can be selected in a wide range, and for example it can be 20-1000 $m^2/g$. Said carbon nanotube can be commercially available or prepared according to the methods as disclosed in the literatures, which are well known in the art and will not be detailed herein.

In a further preferable embodiment of the present invention, said solid carbon source is a multi-walled carbon nanotube, and said multi-walled carbon nanotube has a specific surface area of 50-500 $m^2/g$, preferably 100-400 $m^2/g$.

Said solid carbon source can also contain an oxygen element, a nitrogen element and other non-metal elements (such as a phosphorus atom and a sulfur atom), or be free of the oxygen element, the nitrogen element and other non-metal elements (such as a phosphorus atom and a sulfur atom).

According to the process of the present invention, in case that said solid carbon source contains the oxygen element, the content of the oxygen element is generally ≤2 wt %, preferably ≤0.5 wt %.

According to the process of the present invention, in case that said solid carbon source contains the nitrogen element, the content of the nitrogen element is generally ≤0.5 wt %, preferably ≤0.2 wt %.

According to the process of the present invention, in case that said solid carbon source contains other non-metal elements (such as the phosphorus atom and the sulfur atom), the total content of other non-metal heteroatoms except for the oxygen atom and the nitrogen atom (such as the phosphorus atom and the sulfur atom) in said solid carbon source (calculated as element) is generally ≤0.5 wt %, preferably ≤0.2 wt %.

According to the process of the present invention, said solid carbon source, depending on the sources, can contain some residual metal elements, which are from the catalysts that are used in the preparation of the solid carbon source. These residual metal elements are generally the transition metal elements, and their content is generally 2 wt % or lower, preferably ≤0.5 wt %.

Said magnesium source can be various magnesium-containing substances, preferably said magnesium source is a soluble magnesium source, for example, said magnesium source can include at least one of magnesium nitrate, magnesium nitrite, magnesium oxalate, magnesium oxide, magnesium hydroxide, magnesium sulfate, magnesium sulfite, magnesium tartrate, magnesium sulfide, magnesium cyanide, magnesium thiosulfate, magnesium rhodanate, magnesium iodide, magnesium chloride, magnesium bromide, magnesium acetate and magnesium carbonate.

Said chlorine source can be various chlorine-containing substances, for example, said chlorine source can comprise at least one of chlorine gas, magnesium chloride, hydrogen chloride, hypochlorous acid, magnesium hypochlorite, chloric acid, magnesium chlorite, perchloric acid and magnesium perchlorite.

Said magnesium source and said chlorine source can comprise the same substance, for example, said magnesium source can contain magnesium chloride, and said chlorine source can also contain magnesium chloride. According to a particularly preferable embodiment of the present invention, both of said magnesium source and said chlorine source contain magnesium chloride, and said magnesium source further contains a magnesium-containing and chlorine-free substance (e.g. magnesium nitrate), or said chlorine source further contains a chlorine-containing and magnesium-free substance (e.g. ammonium chloride). Magnesium chloride can be used in form of magnesium chloride hexahydrate and/or anhydrous magnesium chloride.

In another aspect, the present invention also provides a carbonaceous material prepared by the above process.

Based on the total weight of the carbonaceous material, the carbonaceous material contains 1-99 wt % of a carbon element, 0.2-60 wt % of a magnesium element, 0.5-60 wt % of an oxygen element and 0.1-40 wt % of a chlorine element; wherein in the XPS spectrum of said carbonaceous material, the binding energy characteristic peak of the 2 p electron of magnesium is located at >50.3 eV; preferably, based on the total weight of the carbonaceous material, the carbonaceous material contains 10-90 wt % of a carbon element, 2-50 wt % of a magnesium element, 2-50 wt % of an oxygen element and 1-30 wt % of a chlorine element; more preferably, based on the total weight of the carbonaceous material, the carbonaceous material contains 20-80 wt % of a carbon element, 5-30 wt % of a magnesium element, 5-40 wt % of an oxygen element and 2-20 wt % of a chlorine element; further preferably, based on the total weight of the carbonaceous material, the carbonaceous material contains 25-41 wt % of a carbon element, 20-30 wt % of a magnesium element, 19-40 wt % of an oxygen element and 4-20 wt % of a chlorine element.

Preferably, said carbonaceous material can have at least one structure selected from carbon nanotube, active carbon, graphite, graphene, fullerene, nano-carbon particle, active carbon, thin-layer graphite, nano-carbon fiber and nano-adamas.

Preparation Process 2

The present invention also provides a process for preparing a carbonaceous material, wherein said process includes the following steps: (1) contacting a starting carbonaceous material with a Grignard reagent in an inactive atmosphere; (2) removing the excessive Grignard reagent with a solvent; and (3) drying the substance obtained in Step (2). According to an embodiment of the present invention, the starting carbonaceous material contains an oxygen element.

The present invention also provides a process for preparing a carbonaceous material, which comprises: (1) contacting a starting carbonaceous material with a Grignard reagent in an inactive atmosphere for ≥1 hours, e.g. 2-24 hours; (2) removing the excessive Grignard reagent by a solvent-washing; and (3) drying to produce said carbonaceous material.

According to the process for preparing the carbonaceous material of the present invention, said in Step (1), the Grignard reagent is contacted with the starting carbonaceous material in an inactive atmosphere to treat the starting carbonaceous material. Said starting carbonaceous material (also called herein as the solid carbon source) contains the oxygen element. For example the content of the oxygen element of the starting carbonaceous material can be 5-40 wt %, e.g. 5-35 wt %, 5-30 wt %, preferably 5-25 wt %, further preferably 5-20 wt %. In an embodiment, the starting carbonaceous material has a peroxy group content of ≥0.5× $10^{-6}$ mol/g, e.g. $0.5 \times 10^{-6}$ mol/g to $500 \times 10^{-6}$ mol/g, e.g. ≥$1 \times 10^{-6}$ mol/g or ≥$2 \times 10^{-6}$ mol/g.

The starting carbonaceous material (also called herein as the solid carbon source) is carbon material having a function of catalytic oxidative dehydrogenation of hydrocarbons and containing the oxygen element, and can be at least one of an oxygen-containing carbon nanotube, an oxygen-containing fullerene, an oxygen-containing active carbon, an oxygen-containing nano-carbon particle, an oxygen-containing nano-carbon fiber and an oxygen-containing nano-adamas. Preferably, said starting carbonaceous material comprises an oxygen-containing carbon nanotube and/or an oxygen-containing active carbon. Said oxygen-containing carbon nanotube can comprise an oxygen-containing single-walled carbon nanotube and/or an oxygen-containing multi-walled carbon nanotube. Said oxygen-containing carbon nanotube can have a specific surface area of 10-300 $m^2$/g.

Said starting carbonaceous material can contain the oxygen element. This starting carbonaceous material can be commercially available or prepared by introducing the oxygen element to an oxygen-free carbonaceous material (having an oxygen content of <0.1 wt %) or prepared by oxidation of a low-oxygen-content carbon material (the carbonaceous material is also called as carbon material) to further introduce the oxygen element. For example, the oxygen element can be introduced by calcining an oxygen-free carbonaceous material in an oxygen atmosphere, or the oxygen element can be introduced by contacting an oxygen-free carbonaceous material with an oxidative strong acid. Alternatively, an oxygen-containing carbonaceous material with the increased oxygen content can be obtained by calcining the low-oxygen-content carbonaceous material in presence of oxygen gas, or by contacting the low-oxygen-content carbonaceous material and an oxidative strong acid to introduce the oxygen element. Said oxidative strong acid is for example sulfuric acid and/or nitric acid. Said oxidative strong acid is preferably a mixed oxidative strong acid formed by mixing sulfuric acid and nitric acid in a volume ratio of (1-4):1. Said oxygen-free carbonaceous material is for example one or more of carbon nanotube, fullerene, active carbon, nano-carbon particle, nano-carbon fiber and nano-adamas. Preferably, said oxygen-free carbonaceous material comprises carbon nanotube and/or active carbon. Said carbon nanotube can have a specific surface area of 10-300 m²/g. Said oxygen-free carbonaceous material can be commercially available and can be prepared according to the well-known methods. For example, the carbon nanotube can be prepared according to the method as disclosed *Mechanical Engineering Materials*, 2003, 27 (11): 33. Said low-oxygen-content carbon material can be one or more of an oxygen-containing carbon nanotube with a low-oxygen-content, an oxygen-containing fullerene with a low-oxygen-content, an oxygen-containing active carbon with a low-oxygen-content, an oxygen-containing nano-carbon particle with a low-oxygen-content, an oxygen-containing nano-carbon fiber with a low-oxygen-content and an oxygen-containing nano-adamas with a low-oxygen-content, all of which have an oxygen content lower than that of the starting carbonaceous material being produced by oxidation of said low-oxygen-content carbon material. Said starting carbonaceous material (solid carbon source) can have an oxygen element content of 5-40 wt %, preferably 5-30 wt %, e.g. 5-25 wt %, further preferably 5-20 wt %. Said starting carbonaceous material can have a carbon element content of 50-95 wt %, e.g. 60-95 wt %, 70-95 wt %, 75-94 wt % or 80-90 wt %. In an embodiment, in the starting carbonaceous material, the sum of the carbon content and the oxygen content is ≥90 wt %, e.g. 90-99.5 wt %, e.g. 90-100 wt % or 90-99.5 wt % or 95-99 wt %. The starting carbonaceous material can further contain a hydrogen element, and the content of the hydrogen element is preferably ≤5 wt %, e.g. 0-5 wt %, 0.1-4 wt % or 0.5-2 wt %.

In an embodiment, the starting carbonaceous material is obtained by oxidation of an oxygen-free carbonaceous material and/or a low-oxygen-content carbonaceous material, wherein said oxidation is conducted with oxygen gas and/or an oxidative strong acid. The oxygen content after oxidation of said oxygen-free carbonaceous material and/or said low-oxygen-content carbonaceous material is at least 0.1 wt %, e.g. 0.2-30 wt %, 1-25 wt %, 2-20 wt %, 4-19 wt %, 1-5 wt % or 5-10 wt % higher than the oxygen content before oxidation. Said oxygen-free carbonaceous material has an oxygen content of ≤0.1 wt % and a carbon content of preferably ≥95 wt %, e.g. 95-99.9 wt %. Said low-oxygen-content carbonaceous material has an oxygen content of 0.1-38 wt %, e.g. 0.2-38 wt % or 1-35 wt % or 2-30 wt % or 3-25 wt % or 4-20 wt % or 5-15 wt % or 6-10 wt % or 0.5-7 wt %, 0.1-5 wt % or 1-5 wt %. The oxidation with oxygen gas is generally conducted by calcining the oxygen-free carbonaceous material in an oxygen gas-containing atmosphere. The calcination temperature can be forexample 350-480° C., and the calcination time can be for example 2-100 hours. The oxygen gas-containing atmosphere can have an oxygen gas content of e.g. 5-30 vol %. Said oxygen gas-containing atmosphere is for example the air. Said oxidation with the oxidative strong acid can be conducted by contacting the oxygen-free carbonaceous material and/or the low-oxygen-content carbonaceous material with the oxidative strong acid at 0-90° C., e.g. at room temperature for 2-100 hours. The contacting is preferably conducted under stirring, e.g. mechanical stirring and/or ultra-sonication action.

The Grignard reagent has a formula of RMgX, wherein R can be an aromatic group or an alkyl group, and X is at least one halogen element, e.g. F, Cl, Br, or I, such as F, Cl, or Br, preferably Cl. In Step (1), said Grignard reagent can be one or more of the Grignard reagent having the above formula.

According to the process for preparing the carbonaceous material of the present invention, said inactive atmosphere refers to such an atmosphere, in which the gas in said atmosphere does not react with the Grignard reagent in the contacting condition of Step (1) to convert the Grignard reagent to other substances. The gas in said inactive atmosphere is for example one or more of nitrogen, argon, and helium.

The process for preparing the carbonaceous material according to the present invention comprises, in Step (1), contacting a starting carbonaceous material with a Grignard reagent to carry out the reaction, wherein the starting carbonaceous material can be directly contacted with the Grignard reagent, for example contacted with a Grignard reagent that is not dissolved in a solvent or a pure Grignard reagent, or the starting carbonaceous material can be contacted with the Grignard reagent in the presence of a solvent. The mole ratio of the Grignard reagent to the oxygen in the starting carbonaceous material (solid carbon source) is preferably 0.01-10, e.g. 0.1-9, 0.3-8, 0.7-7, 1-7 or 1.5-7, more preferably 0.1-5, e.g. 0.5-2. Preferably, the starting carbonaceous material and the Grignard reagent are contacted in the presence of a solvent, wherein the weight ratio of the solvent to the starting carbonaceous material is preferably ≤30:1, e.g. 7-30:1, preferably 10-20:1. In an embodiment, the weight ratio of the starting carbonaceous material:the Grignard reagent:the solvent is 1:0.002-0.3:2-30; in the mixture consisting of the starting carbonaceous material, the Grignard reagent and the solvent, the content of the starting carbonaceous material is 20-200 g/L, preferably 40-150 g/L, the mole ratio of the Grignard reagent to the oxygen in the carbonaceous material is preferably 1-20:1.

The temperature of contacting the Grignard reagent with the starting carbonaceous material is not particularly limited according to the present invention, and is generally 0-200° C., e.g. room temperature (said room temperature can be 15-40° C.). In case that the contacting is conducted in the presence of a solvent, the contacting temperature is preferably such a temperature, at which the solvent is in the liquid state, generally higher than the freezing point of the solvent and lower than the freezing point of the solvent. The contacting pressure is not particularly limited according to the present invention, and is generally the normal pressure, e.g. the atmospheric pressure or 0.5-1.1 atm. The contacting time can be preferably ≥1 hour, for example, 1.5-150 hours, 2-100 hours, 2-50 hours, 4-30 hours, 8-28 hours or 2-24 hours.

According to the process for preparing the carbonaceous material of the present invention, in Step (2) (i.e. washing), the Grignard reagent that has been unreacted with the carbonaceous material is dissolved in the solvent. For example, the carbonaceous material that has been contacted with the Grignard reagent, obtained in Step (1), is mixed with the solvent, and the resulting mixture is filtered. Said Step (2) can be repeated for one or more times, for example 3-5 times, so that the Grignard reagent unreacted with the carbonaceous material is dissolved. The used amount of the solvent for each washing is not particularly limited. For example, the weight ratio of the solvent used in the washing to the carbonaceous material is 2-20:1 or 5-10:1. Said solvent is such an organic solvent in which Grignard reagent is soluble, e.g. an ether and/or tetrahydrofuran. Said ether is preferably a lower ether having a carbon atom number of 8 or lower, e.g. one or more of ethers having a carbon atom number of 2-8 in the molecule, preferably diethylether and/or tetrahydrofuran.

According to the preparation process for the carbonaceous material of the present invention, in Step (3), the purpose of the drying is to remove the solvent in the carbonaceous material. The drying can be done in an inactive atmosphere, or in an oxygen-containing atmosphere, or successively in an inactive atmosphere and in an oxygen-containing atmosphere, wherein said inactive atmosphere refers to an atmosphere formed from an inactive gas. For example, said inactive gas is a gas of Group 18 (such as helium, neon, argon) and/or nitrogen. Preferably, said drying is preferably conducted in an inactive atmosphere. The drying temperature can be selected in a wide range. For example, the drying temperature is 20-200° C., preferably 60-120° C. The drying can be followed by a natural cooling, for example to room temperature. Room temperature can be 15-40° C.

In an aspect, the present invention also provides the use of the above carbonaceous material in catalytic oxidation of hydrocarbons.

Said hydrocarbon can have a carbon atom number of 2-15, preferably 2-12, and said hydrocarbon comprises at least one of an alkane, an alkene and an aromatic hydrocarbon containing alkyl group(s); said alkyl contains at least two carbon atoms.

Said hydrocarbon can comprise at least one of ethane, propane, butane, pentane, hexane, heptane, octane, nonane, decane, undecane, dodecane, ethylbenzene, propylbenzene, butylbenzene, pentylbenzene and hexylbenzene; preferably, said hydrocarbon comprises at least one of butane, 1-butene, ethylbenzene, propane, ethane and pentane.

The mole ratio of hydrocarbon to oxygen can be selected in a wide range, for example, (0.01-100):1, preferably (0.1-10):1, more preferably (0.2-5):1.

The gas containing hydrocarbons and oxygen can further contain a carrier gas. Said carrier gas can be those conventionally used in the oxidative dehydrogenation of hydrocarbons. For example, said carrier gas comprises at least one of nitrogen, $CO_2$ and water vapor.

In the gas containing hydrocarbons and oxygen, the total concentration of hydrocarbons and oxygen can be those conventionally in the field of oxidative dehydrogenation of hydrocarbons, and for example, 0.5-70 vol %. Preferably, in the gas containing hydrocarbons and oxygen, the total concentration of hydrocarbons and oxygen is 1-50 vol %, more preferably 2-30 vol %.

The condition for catalytic oxidation of hydrocarbons can be those conventionally in the field of oxidation of hydrocarbons. For example, the condition for catalytic oxidation of hydrocarbons can comprise: the contacting temperature can be 200-650° C., preferably 300-600° C., more preferably 350-550° C., more further preferably 400-450° C.; the pressure can be 0.05-80 MPa, preferably 0.1-60 MPa, more preferably 1-50 MPa, more further preferably 5-45 MPa; based on the total volume of the gas containing hydrocarbons and oxygen, the volume space velocity for the gas passing through the catalyst can be 0.1-10000 preferably 1-6000 $V^-$, more preferably 5-5000 $h^-$, more further preferably 10-4000 $h^-$.

The contacting for catalytic oxidation of hydrocarbons can be conducted in a fixed bed reactor and/or a fluidized bed reactor, preferably a fixed bed reactor, more preferably a tube-type fixed bed reactor. Preferably, said carbonaceous material, used as catalyst, is packed in said tube-type fixed bed reactor, and the gas containing hydrocarbons and oxygen is passed through said tube-type fixed bed reactor to conduct the contacting.

The present invention also provides the use of said carbonaceous material in the catalytic oxidative dehydrogenation of hydrocarbons. Said use generally comprises a step of contacting a mixed gas containing hydrocarbons, a carrier gas and oxygen gas with said carbonaceous material in an oxidative dehydrogenation. Said hydrocarbon can have a carbon atom number of 2-12. Said hydrocarbon comprises at least one of an alkane, an alkene and a non-benzene aromatic hydrocarbon. Preferably, said hydrocarbon comprises at least one of butane, 1-butene, ethylbenzene, propane, ethane and pentane. The condition for oxidative dehydrogenation of hydrocarbons can be the conventional conditions in catalytic oxidative dehydrogenation of lower alkanes. For example, the reaction temperature can be 350-550° C., the concentration of hydrocarbons can be 1-3 vol %, and the mole ratio of hydrocarbon to oxygen gas can be (0.2-3):1.

The carrier gas can be a carrier gas conventionally used in oxidative dehydrogenation of hydrocarbons, for example, one of nitrogen, $CO_2$ and water, e.g. nitrogen.

EXAMPLES

The present invention will be further illustrated with the following examples. In the following Examples and Comparative Examples, all of the agents are commercially available analytically pure agents, unless indicated to the contrary.

In the following Examples and Comparative Examples, the XPS analysis was carried out with an ESCALab250 type X-ray photoelectron spectroscoper (Thermo Scientific Company). The excitation source was a monochromatic Al Kα X-ray, the energy was 1486.6 eV, the power was 150 W, and the pass energy for narrow scan was 30 eV. The basis vacuum for analysis and test was $6.5 \times 10^{-10}$ mbar. The electron binding energy was corrected with the C1s peak (284.0 eV) of the simple substance of carbon. The relevant data was treated with the ThermoAvantage software (version no. V5.926) accompanied along with the X-ray photoelectron spectroscoper. The quantitative analysis was carried out in the analysis module with the sensitivity factor method well known in the art. The samples were dried for 3 hours at 150° C. and 1 atm in a helium atmosphere before the test.

In the following Examples and Comparative Examples, the thermogravimetric analysis was conducted with the TA5000 thermal analyzer. The test conditions included an air atmosphere, a temperature rising speed of 10° C./min, and a temperature range of room temperature (25° C.) to 1000° C. The samples were dried for 3 hours at 150° C. and 1 atm in a helium atmosphere before the test.

In the following Examples and Comparative Examples, the specific surface area was measured with ASAP 2000-type N2 physical adsorption analyzer (Micromertrics Company, USA).

In the following Examples and Comparative Examples, the X-ray micro zone elemental analysis was done with a scanning electron microscope-energy spectrum analysis instrument to determine the distribution uniformity of the magnesium element on the surface of the carbonaceous material. The specific measurement method was as follows: the carbon nanotube having a length in a range of 25-250 nm was scanned with an energy spectrum analysis instrument in the length direction to determine the concentration or content of the magnesium atoms in said length direction (wherein five concentrations were measured). Five samples prepared from the same nano-carbon material were subjected to the scanning electron microscope-energy spectrum analysis, and five different carbon nanotubes for each sample were scanned. 25 magnesium atom concentrations were obtained and the corresponding coefficient of variation for the magnesium atom concentrations was calculated. The coefficient of variation was a percent of the standard deviation of 25 measurement values relative to the mean number of said 25 measurement values, i.e. the coefficient of variation CV=(standard deviation SD/mean number MN)×100%.

In the following Examples and Comparative Examples, the content of the peroxy group in the sample was measured with the iodometric method, in which 0.3 g of the carbon material sample to be measure was added to a solution consisting of 10 mL KI (100 g/L), 5 mL $H_2SO_4$ (0.1 mol/L), 30 mL deionized water and 3 drops of $(NH_4)_6Mo_7O_{24}$ (30 g/L), the resulting mixture was ultrasonically treated in darkness at 25° C. for 30 minutes to complete the reaction (1); the resulting mixture was filtered and washed with deionized water for 5 times, all of the filtrates were collected and titrated with a $Na_2S_2O_3$ (0.002 mol/L) solution to determine the iodine content, as shown in the reaction (2). The concentration of the peroxy group was calculated based on the formula (3), wherein c(peroxide) (mol/g), V (mL) and m (g) respectively represented the concentration of the peroxy group, the volume of the consumed $Na_2S_2O_3$ solution and the mass of the added carbon material to be measured.

$O_2^{2-}$-2KI+2$H_2SO_4$→$O^{2-}$+2-+$I_2$+2$KHSO_4$+$H_2O$   Reaction (1):

$I_2$+2$Na_2S_2O_3$→2NaI+$Na_2S_4O_6$   Reaction (2)

c(peroxide)=2×10$^{-6}$·V/m   Formula (3)

In the following Examples and Comparative Examples, the oxygen-free carbon nanotube had a carbon content of >95 wt %, an ash content of <1.5 wt %, and a specific surface area of 123 m$^2$/g, and was commercially available from Shandong Dazhan Nano Material Co. Ltd.;

the oxygen-containing carbon nanotube had a carbon content of >95 wt %, an oxygen content of 1.1 wt %, an ash content of <1.2 wt %, and a specific surface area of 211 m$^2$/g, and was commercially available from Chengdu Organic Chemicals Co. Ltd., Chinese Academy of Sciences; graphene had a carbon content of >99 wt %, an ash content of <0.8 wt %, and a specific surface area of 627 m$^2$/g, and was commercially available from Chengdu Organic Chemicals Co. Ltd., Chinese Academy of Sciences.

Example 1

At room temperature (25° C.), a solid carbon source (an oxygen-free carbon nanotube), a precursor (magnesium chloride hexahydrate) and water were mixed under stirring for 6 hours to produce a mixture, wherein the weight ratio of the carbon element in said solid carbon source to the magnesium element in said precursor was 1:0.5, the weight ratio of the carbon element in said solid carbon source to the chlorine element of said precursor was 1:1.48, the weight ratio of water to the solid carbon source was 40:1. The obtained mixture was dried, the drying temperature was 120° C., until the mixture reached the constant weight (the drying time was 6 hours) to produce a dried mixture. The resulting dried mixture was then calcined at 330° C. in air for 2 hours, and then calcined at 430° C. in air for 2 hours to produce the carbonaceous material of this Example.

Example 2

At room temperature (25° C.), a solid carbon source (an oxygen-free carbon nanotube), a precursor (a mixture of magnesium chloride hexahydrate and magnesium nitrate) and water were mixed under stirring for 6 hours to produce a mixture, wherein the weight ratio of the carbon element in said solid carbon source to the magnesium element in said precursor was 1:1, the weight ratio of the carbon element in said solid carbon source to the chlorine element of said precursor was 1:0.1, the weight ratio of water to the solid carbon source was 50:1. The obtained mixture was dried, the drying temperature was 120° C., until the mixture reached the constant weight (the drying time was 6 hours) to produce a dried mixture. Then the resulting dried mixture was calcined at 300° C. in air for 2 hours, and then calcined at 400° C. in air for 2 hours to produce the carbonaceous material of this Example.

Example 3

At room temperature (25° C.), a solid carbon source (an oxygen-free carbon nanotube), a precursor (a mixture of ammonium chloride and magnesium nitrate) and water were mixed under stirring for 6 hours to produce a mixture, wherein the weight ratio of the carbon element in said solid carbon source to the magnesium element in said precursor was 1:0.01, the weight ratio of the carbon element in said solid carbon source to the chlorine element of said precursor was 1:10, the weight ratio of water to the solid carbon source was 10:1. The obtained mixture was dried, the drying temperature was 120° C., until the mixture reached the constant weight (the drying time was 6 hours) to produce a dried mixture. Then the resulting dried mixture was calcined at 350° C. in air for 2 hours, and then calcined at 450° C. in air for 2 hours to produce the carbonaceous material of this Example.

Example 4

At room temperature (25° C.), a solid carbon source (an oxygen-free carbon nanotube), a precursor (a mixture of magnesium chloride hexahydrate and magnesium nitrate) and water were mixed under stirring for 6 hours to produce a mixture, wherein the weight ratio of the carbon element in said solid carbon source to the magnesium element in said precursor was 1:2, the weight ratio of the carbon element in said solid carbon source to the chlorine element of said precursor was 1:0.01, the weight ratio of water to the solid carbon source was 80:1. The obtained mixture was dried, the drying temperature was 120° C., until the mixture reached the constant weight (the drying time was 6 hours) to produce a dried mixture. The resulting dried mixture was then calcined at 330° C. in air for 2 hours, and then calcined at 380° C. in air for 2 hours to produce the carbonaceous material of this Example.

Example 5

At room temperature (25° C.), a solid carbon source (an oxygen-free carbon nanotube), a precursor (a mixture of concentrated HCl and magnesium oxide) and water were mixed under stirring for 6 hours to produce a mixture, wherein the weight ratio of the carbon element in said solid carbon source to the magnesium element in said precursor was 1:0.002, the weight ratio of the carbon element in said solid carbon source to the chlorine element of said precursor was 1:20, the weight ratio of water to the solid carbon source was 100:1. The obtained mixture was dried, the drying temperature was 120° C., until the mixture reached the constant weight (the drying time was 6 hours) to produce a dried mixture. Then the resulting dried mixture was calcined at 350° C. in air for 2 hours, and then calcined at 450° C. in air for 2 hours to produce the carbonaceous material of this Example.

Example 6

The carbonaceous material was prepared in the same manner as Example 1, except that the resulting dried mixture was calcined at 330° C. in air for 4 hours.

Example 7

The carbonaceous material was prepared in the same manner as Example 1, except that the resulting dried mixture was calcined at 430° C. in air for 4 hours.

Example 8

The carbonaceous material was prepared in the same manner as Example 1, except that the resulting dried mixture was calcined at 210° C. in air for 4 hours.

Example 9

The carbonaceous material was prepared in the same manner as Example 1, except that the resulting dried mixture was calcined at 500° C. in air for 4 hours.

Example 10

The carbonaceous material was prepared in the same manner as Example 1, except that the solid carbon source was an oxygen-containing carbon nanotube, and the calcination was conducted in argon.

Example 11

The carbonaceous material was prepared in the same manner as Example 1, except that the solid carbon source is graphene.

Comparative Example 1

At room temperature (25° C.), a solid carbon source (an oxygen-free carbon nanotube), a precursor (magnesium chloride hexahydrate) and water were mixed under stirring for 6 hours to produce a mixture, wherein the weight ratio of the carbon element in said solid carbon source to the magnesium element in said precursor was 1:0.5, the weight ratio of the carbon element in said solid carbon source to the chlorine element of said precursor was 1:1.5, the weight ratio of water to the solid carbon source was 40:1. The obtained mixture was dried, the drying temperature was 120° C., until the mixture reached the constant weight (the drying time was 6 hours) to produce a dried mixture. The resulting dried mixture was used as the carbonaceous material of this Comparative Example.

Comparative Example 2

At room temperature (25° C.), a solid carbon source (an oxygen-free carbon nanotube), a precursor (magnesium nitrate hexahydrate) and water were mixed under stirring for 6 hours to produce a mixture, wherein the weight ratio of the carbon element in said solid carbon source to the magnesium element in said precursor was 1:0.5, the weight ratio of water to the solid carbon source was 40:1. The obtained mixture was dried, the drying temperature was 120° C., until the mixture reached the constant weight (the drying time was 6 hours) to produce a dried mixture. The resulting dried mixture was used as the carbonaceous material of this Comparative Example.

Comparative Example 3

At room temperature (25° C.), a solid carbon source (an oxygen-free carbon nanotube), magnesium oxide powder, ammonium chloride and water were mixed under stirring for 6 hours to produce a mixture, wherein the weight ratio of the carbon element in said solid carbon source to the magnesium element of the magnesium oxide powder was 1:0.5, the weight ratio of the carbon element in said solid carbon source to the chlorine element of the ammonium chloride was 1:1.5, the weight ratio of water to the solid carbon source was 40:1. The obtained mixture was dried, the drying temperature was 120° C., until the mixture reached the constant weight (the drying time was 6 hours) to produce a dried mixture. The resulting dried mixture was then calcined at 330° C. in air for 2 hours, and then calcined at 430° C. in air for 2 hours. The resulting calcined mixture was used as the carbonaceous material of this Comparative Example.

Comparative Example 4

At room temperature (25° C.), a solid carbon source (an oxygen-free carbon nanotube), a precursor (magnesium nitrate hexahydrate) and water were mixed under stirring for 6 hours to produce a mixture, wherein the weight ratio of the carbon element in said solid carbon source to the magnesium element in said precursor was 1:0.5, the weight ratio of water to the solid carbon source was 40:1. The obtained mixture was dried, the drying temperature was 120° C., until the mixture reached the constant weight (the drying time was 6 hours) to produce a dried mixture. The resulting dried mixture was then calcined at 330° C. in air for 2 hours, and then calcined at 430° C. in air for 2 hours. The resulting calcined mixture was used as the carbonaceous material of this Comparative Example.

Comparative Example 5

At room temperature (25° C.), a solid carbon source (graphene), a precursor (magnesium nitrate hexahydrate) and water were mixed under stirring for 6 hours to produce a mixture, wherein the weight ratio of the carbon element in said solid carbon source to the magnesium element in said precursor was 1:0.5, the weight ratio of water to the solid carbon source was 40:1. The obtained mixture was dried, the drying temperature was 120° C., until the mixture reached the constant weight (the drying time was 6 hours) to produce a dried mixture. The resulting dried mixture was then calcined at 330° C. in air for 2 hours, and then calcined at 430° C. in air for 2 hours. The resulting calcined mixture was used as the carbonaceous material of this Comparative Example.

Comparative Example 6

At room temperature (25° C.), a solid carbon source (an oxygen-containing carbon nanotube), a precursor (magnesium nitrate hexahydrate) and water were mixed under stirring for 6 hours to produce a mixture, wherein the weight ratio of the carbon element in said solid carbon source to the magnesium element in said precursor was 1:0.5, the weight ratio of water to the solid carbon source was 40:1. The obtained mixture was dried, the drying temperature was 120° C., until the mixture reached the constant weight (the drying time was 6 hours) to produce a dried mixture. The resulting dried mixture was then calcined at 330° C. in air for 2 hours, and then calcined at 430° C. in air for 2 hours. The resulting calcined mixture was used as the carbonaceous material of this Comparative Example.

Test Example 1

The carbonaceous materials obtained in Examples 1-11 and Comparative Examples 1-6 were subjected to the XRF elemental analysis, the XPS analysis, the transmission electron microscope analysis, and the transmission electron microscope-based X-ray micro zone element quantitative analysis.

Figure 1:
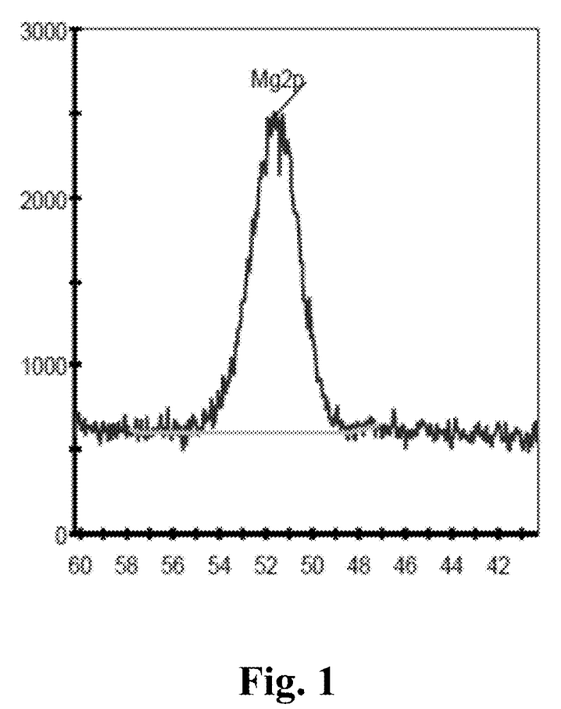
FIG. 1 is an XPS spectrum for Mg of the carbonaceous material obtained in Example 1, wherein the vertical axis represents the signal value, and the lateral axis represents the binding energy (eV).

FIG. 1 was an XPS spectrum for magnesium of the carbonaceous material obtained in Example 1, wherein the vertical axis represents the signal value, and the lateral axis represents the binding energy (eV(±0.2 eV)).

Figure 2:
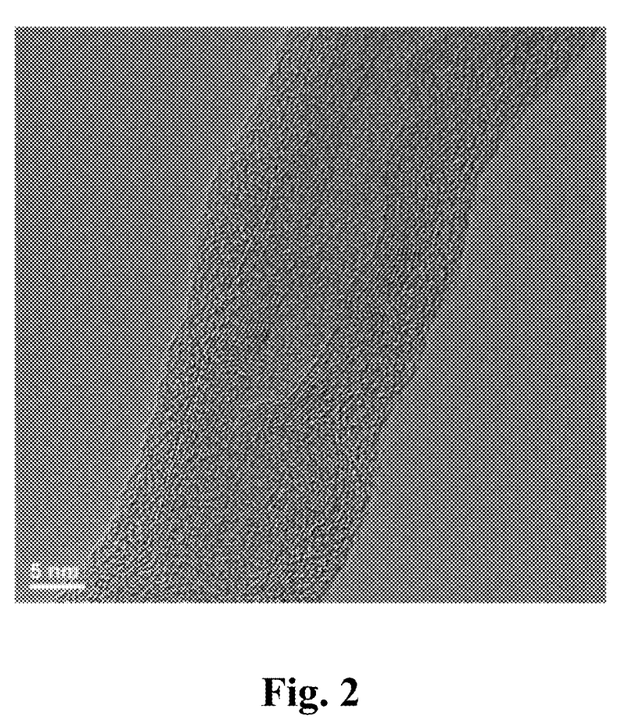
FIG. 2 is a transmission electron microscope photo of the carbonaceous material obtained in Example 1.

FIG. 2 was a transmission electron microscope photo of the carbonaceous material obtained in Example 1.

The results of the XRF elemental analysis and the XPS analysis were shown in Table 1. In the "XPS Analysis" column of Table 1, "Mg" represented the location of the binding energy characteristic peak of the 2 p electron of magnesium (eV(±0.2 eV)), "O" represented the ratio of the signal value of oxygen at 533.33 eV(±0.2 eV) to the signal value of oxygen at 531.96 eV(±0.2 eV), "Cl" represented the ratio of the signal value of chlorine at 197.94 eV(±0.2 eV) to the signal value of chlorine at 199.93 eV(±0.2 eV), and "Mg-EDS" represented the coefficient of variation for the magnesium element contents (CV %) in different X-ray micro zones having the same area of 25 nm$^2$ in the surface of the carbonaceous material.

It could be seen from the comparison based on Examples 1-11 and Comparative Examples 1-6 that the incorporation of chlorine and the calcination resulted in that the binding energy characteristic peak of the 2 p electron of magnesium was located at >50.3 eV in the XPS of the carbonaceous material according to the present invention, and the coefficient of variation for the magnesium element content in the different X-ray micro zones having the same area in the surface of the carbonaceous material according to the present invention was 20% or lower.

Test Example 2

0.2 g of the carbonaceous materials obtained in Examples 1-11 and Comparative Examples 1-6, used as catalyst, were respectively packed in a universal fixed-bed micro-quartz tube reactor. The micro-quartz tube reactor was blocked with quartz sand at both ends. The gas containing hydrocarbons and oxygen (the concentration of butane was 1.98 vol %, the mole ratio of butane to oxygen was 0.5:1, the balance was nitrogen) was reacted at 0.1 MPa under 450° C. at a total volume space velocity of 1000 h$^{-1}$. After 8 hours of the reaction, the butane conversion, the butadiene selectivity and the total olefin selectivity were measured, and the butadiene yield and the total olefin yield were calculated. The results were listed in Table 2.

TABLE 2

| | Catalytic capability | | | | |
|---|---|---|---|---|---|
| Carbonaceous material | Butane conversion % | Butadiene selectivity % | Total olefin selectivity % | Butadiene yield % | Total olefin yield % |
| Example 1 | 26.5 | 15.5 | 47.8 | 4.1 | 12.7 |
| Example 2 | 23.6 | 18.9 | 56.4 | 4.5 | 13.3 |
| Example 3 | 25.6 | 14.2 | 46.3 | 3.6 | 11.9 |
| Example 4 | 22.0 | 12.6 | 35.8 | 2.8 | 7.9 |
| Example 5 | 15.6 | 18.5 | 49.2 | 2.9 | 7.7 |

TABLE 1

| Carbonaceous material | Weight ratio in starting material | | | | Elemental analysis (wt %) | | | | XPS Analysis | | | Mg-EDS, CV % | Peroxy group contents/(10$^{-6}$ mol/g) |
|---|---|---|---|---|---|---|---|---|---|---|---|---|---|
| | C | Mg | O | Cl | C | Mg | O | Cl | Mg | O | Cl | | |
| Example 1 | 1 | 0.5 | 0 | 1.48 | 40.19 | 23.82 | 19.83 | 16.15 | 51.25 | 0.83 | 0.88 | 16 | 0.654 |
| Example 2 | 1 | 1 | 0 | 0.1 | 26.65 | 29.81 | 39.42 | 4.11 | 50.67 | 0.40 | 1.03 | 14 | 0.564 |
| Example 3 | 1 | 0.01 | 0 | 10 | 76.21 | 5.1 | 6.85 | 11.61 | 50.61 | 0.51 | 2.31 | 16 | 0.872 |
| Example 4 | 1 | 2 | 0 | 0.01 | 25.62 | 50.64 | 22.38 | 1.31 | 50.62 | 0.67 | 2.12 | 18 | 1.768 |
| Example 5 | 1 | 0.002 | 0 | 20 | 60.51 | 0.51 | 6.13 | 32.31 | 50.5 | 0.44 | 3.36 | 9 | 1.863 |
| Example 6 | 1 | 0.5 | 0 | 1.48 | 42.12 | 25.56 | 20.12 | 11.72 | 51.4 | 0.72 | 1.12 | 14 | 0.732 |
| Example 7 | 1 | 0.5 | 0 | 1.48 | 37.82 | 22.62 | 20.83 | 17.83 | 51.4 | 0.46 | 0.98 | 13 | 0.781 |
| Example 8 | 1 | 0.5 | 0 | 1.48 | 27.56 | 24.87 | 19.81 | 27.32 | 51.2 | 0.83 | 1.21 | 14 | 1.634 |
| Example 9 | 1 | 0.5 | 0 | 1.48 | 35.49 | 22.32 | 27.92 | 13.27 | 50.83 | 0.37 | 0.74 | 14 | 1.874 |
| Example 10 | 1 | 0.5 | 0 | 1.48 | 39.67 | 19.71 | 20.92 | 19.67 | 51.03 | 0.40 | 0.67 | 14 | 0.836 |
| Example 11 | 1 | 0.5 | 0 | 1.48 | 39.33 | 24.01 | 19.85 | 16.11 | 50.78 | 0.43 | 0.77 | 13 | 0.824 |
| Comparative Example 1 | 1 | 0.5 | 0 | 1.48 | 26.1 | 13.05 | 24.12 | 36.51 | 50.06 | 0.10 | 0.12 | 23 | 2.456 |
| Comparative Example 2 | 1 | 0.5 | 0 | 0 | 45.81 | 18.57 | 34.98 | 0 | 50.12 | 0.08 | 0 | 28 | 2.651 |
| Comparative Example 3 | 1 | 0.5 | 0 | 1.48 | 19.31 | 44.32 | 35.73 | 0.05 | 50.04 | 0.06 | 0.13 | 25 | 4.563 |
| Comparative Example 4 | 1 | 0.5 | 0 | 0 | 45.34 | 32.62 | 21.51 | 0 | 49.86 | 0.09 | 0 | 27 | 3.879 |
| Comparative Example 5 | 1 | 0.5 | 0 | 0 | 44.25 | 33.13 | 22.22 | 0 | 50.01 | 0.15 | 0 | 26 | 3.241 |
| Comparative Example 6 | 1 | 0.5 | 0 | 0 | 55.83 | 27.71 | 15.92 | 0 | 50.03 | 0.17 | 0 | 38 | 2.653 |

TABLE 2-continued

| | Catalytic capability | | | | |
|---|---|---|---|---|---|
| Carbonaceous material | Butane conversion % | Butadiene selectivity % | Total olefin selectivity % | Butadiene yield % | Total olefin yield % |
| Example 6 | 23.5 | 13.5 | 48.9 | 3.2 | 11.5 |
| Example 7 | 23.4 | 15.1 | 59.2 | 3.5 | 13.9 |
| Example 8 | 8.1 | 28.5 | 81.5 | 2.3 | 6.6 |
| Example 9 | 10.5 | 23.2 | 74.2 | 2.4 | 7.8 |
| Example 10 | 19.6 | 16.8 | 56.2 | 3.3 | 11.0 |
| Example 11 | 22.9 | 14.1 | 42.4 | 3.2 | 9.7 |
| Comparative Example 1 | 13.5 | 5.8 | 8.5 | 0.8 | 1.1 |
| Comparative Example 2 | 6.7 | 6.8 | 12.8 | 0.5 | 0.9 |
| Comparative Example 3 | 17.5 | 4.3 | 14.1 | 0.8 | 2.5 |
| Comparative Example 4 | 10.1 | 5.1 | 13.1 | 0.5 | 1.3 |
| Comparative Example 5 | 14.9 | 7.1 | 10.8 | 1.1 | 1.6 |
| Comparative Example 6 | 6.4 | 7.1 | 12.5 | 0.5 | 0.8 |

It could be seen from Table 2 that the carbonaceous material of the present invention, used as catalyst, could increase both of the olefin selectivity and the conversion. Furthermore, one preferable carbonaceous material containing 20-80 wt % of a carbon element, 5-30 wt % of a magnesium element, 5-40 wt % of an oxygen element and 2-20 wt % of a chlorine element having a peroxy group content of ≤1×10$^{-6}$ mol/g could further increase the olefin selectivity and the conversion in the oxidation of hydrocarbons. Furthermore, the preferable calcination temperature of 300-450° C. could further increase the olefin selectivity and the conversion in the oxidation of hydrocarbons.

In the following Examples and Comparative Examples, the carbon nanotube (starting carbon nanotube) had a carbon content of >95 wt %, an ash content of <1.5 wt %, and a specific surface area of 160 m$^2$/g, and was commercially available from Institute of Metal Research (IMR), Chinese Academy of Sciences (CAS); the oxygen-containing carbon nanotube had a carbon content of >85 wt %, an oxygen element content of 10 wt %, an ash content of <1.5 wt %, and a specific surface area of 200 m$^2$/g, and was commercially available from IMR, CAS; an oxygen-containing active carbon had an ash content of <0.8 wt %, a specific surface area of 819 m$^2$/g, an oxygen content of 9.53 wt %, and a carbon content of 88.4%, and was commercially available from Chengdu Organic Chemicals Co. Ltd., Chinese Academy of Sciences.

Example A1

(1) 10 g carbon nanotube was added to a beaker containing 500 mL of a mixed acid ($V_{sulfuric\ acid}$:$V_{nitric\ acid}$=3). Then, the beaker was placed in an ultrasonic cleaner and ultrasonically treated for 10 hours. The content in the beaker was washed with deionized water until the filtrate became neutral. Finally, the filter cake was placed and dried in an oven at 120° C. for 12 hours to produce a carbon nanotube (o-CNT) having an oxygen content of about 14 wt %.

(2) 1 g o-CNT was added to a solution of phenylmagnesium chloride in diethylether (20 mL, 1.0M). The resulting mixture was stirred at room temperature (e.g. 25° C.) for 2 hours and refluxed under 1 atm for 12 hours, then washed with diethylether for 4-5 times, and dried at 80° C. for 2 hours to produce the carbonaceous material of the present invention. Said carbonaceous material had a structure of carbon nanotube. The composition, the location of the binding energy characteristic peak of the 2 p electron of magnesium, and the peroxy group content of said carbonaceous material were listed in Table A1.

Example A2

This example was conducted in the same manner as Example A1 except that in Step (2), an active carbon having an oxygen content of 9.53 wt % was used instead of said o-CNT. The resulting carbonaceous material had a structure of active carbon. The composition, the location of the binding energy characteristic peak of the 2 p electron of magnesium, and the peroxy group content of said carbonaceous material were listed in Table A1.

Example A3

This example was conducted in the same manner as Example A1 except that in Step (2), a solution of butylmagnesium chloride in diethylether (1.0M) was added instead of the solution of phenylmagnesium chloride in diethylether. The resulting carbonaceous material had a structure of carbon nanotube. The composition, the location of the binding energy characteristic peak of the 2 p electron of magnesium, and the peroxy group content of said carbonaceous material were listed in Table A1.

Example A4

This example was conducted in the same manner as Example A1 except that in Step (1), 10 g carbon nanotube was calcined in air at 450° C. for 4 hours to produce a carbon nanotube having an oxygen content of 5% (5% o-CNT). The resulting carbonaceous material had a structure of carbon nanotube. The composition, the location of the binding energy characteristic peak of the 2 p electron of magnesium, and the peroxy group content of said carbonaceous material were listed in Table A1.

Example A5

This example was conducted in the same manner as Example A1 except that in Step (2), a solution of benzenemethylmagnesium chloride in diethylether (30 mL, 1.0M) was added instead of the solution of phenylmagnesium chloride in diethylether, and the resulting mixture was refluxed for 24 hours. The resulting carbonaceous material had a structure of carbon nanotube. The composition, the location of the binding energy characteristic peak of the 2 p electron of magnesium, and the peroxy group content of said carbonaceous material were listed in Table A1.

Example A6

This example was conducted in the same manner as Example A1 except that in Step (2), a solution of benzenemethylmagnesium chloride in tetrahydrofuran (20 mL, 1.0M) was added instead of the solution of phenylmagnesium chloride in diethylether, and the resulting mixture was refluxed at 70° C. for 24 hours. The resulting carbonaceous material had a structure of carbon nanotube. The composition, the location of the binding energy characteristic peak of the 2 p electron of magnesium, and the peroxy group content of said carbonaceous material were listed in Table A1.

Comparative Example A1

At room temperature (25° C.), a solid carbon source (an oxygen-free carbon nanotube), a precursor (magnesium nitrate hexahydrate) and water were mixed under stirring for 6 hours to produce a mixture, wherein the weight ratio of the carbon element in said solid carbon source to the magnesium element in said precursor was 1:0.5, the weight ratio of water to the solid carbon source was 40:1. The obtained mixture was dried, the drying temperature was 120° C., until the mixture reached the constant weight (the drying time was 6 hours) to produce a dried mixture. The resulting dried mixture was then calcined at 330° C. in air for 2 hours, and then calcined at 430° C. in air for 2 hours. The resulting calcined mixture was used as the carbonaceous material of this Comparative Example.

Test Examples 0.2 g of the carbonaceous materials obtained in Examples A1-A6 and Comparative Example A1, the direct communicably available starting carbon nanotube, and the oxygen-containing carbon nanotube (o-CNT) obtained in Step (1) of Example A1, used as catalyst, were respectively packed in a universal fixed-bed micro-quartz tube reactor. The micro-quartz tube reactor was blocked with quartz sand at both ends. The gas containing hydrocarbons and oxygen (the concentration of butane was 1.98 vol %, the mole ratio of butane to oxygen was 0.5:1, the balance was nitrogen) was reacted at 0.1 MPa under 450° C. (at 400° C. for active carbon) at a total volume space velocity of 1000 h$^{-1}$. After 8 hours of the reaction, the butane conversion, the butadiene selectivity and the total olefin selectivity were measured. The results were listed in Table 2.

TABLE A2

Catalytic capability of the carbonaceous material

| Carbonaceous material | Catalytic capability | | |
|---|---|---|---|
| | butane conversion/% | butadiene selectivity/% | Total olefin selectivity/% |
| Example A1 | 16.7 | 20.5 | 60 |
| Example A2 | 18 | 17.3 | 60 |
| Example A3 | 21.3 | 14.5 | 67.5 |
| Example A4 | 26.1 | 16.7 | 50.2 |
| Example A5 | 19.6 | 15.7 | 53.6 |
| Example A6 | 21.2 | 13.8 | 48 |
| Starting carbon nanotube | 6.8 | 7.3 | 7.3 |
| o-CNT of Example A1 | 17.0 | 8.9 | 14.6 |
| Comparative Example A1 | 10.1 | 5.1 | 13.1 |

It could be seen from Table A2 that the carbonaceous material of the present invention could produce relatively high conversion, relatively high total olefin selectivity and relatively high butadiene selectivity. The preparation process for the carbonaceous material of the present invention can significantly improve the butadiene selectivity and the total olefin selectivity of the carbonaceous material.

The present invention is described in details with the above preferable embodiments together with the accompanying drawings. However, it should be understood that the present invention is not limited by the minutiae in the above embodiments. Within the technical concepts of the present invention, the various simple modifications can be made to the technical solutions of the present invention, and these simple modifications are within the scope of the present invention.

It should be also understood that various specific technical features described in the above specific embodiments can be combined in any suitable manner without being incompatible with each other. In order to avoid any unnecessary verbosity, all possible combinations are not described herein.

It should be further understood that various embodiments can be combined to form new embodiments in any manner without deviation from the spirits of the present invention, and these new embodiments are considered as being specifically disclosed in the present invention.

The invention claimed is:

1. A carbonaceous material, comprising: based on a total weight of the carbonaceous material, 1-99 wt % of carbon,

TABLE A1

Composition of the carbonaceous material

| Carbonaceous material | Location of the binding energy characteristic peak of the 2 p electron of magnesium, eV | peroxy group content/10$^{-6}$ mol/g | Composition of carbonaceous material | | | | |
|---|---|---|---|---|---|---|---|
| | | | carbon content/wt % | hydrogen content/wt % | oxygen content/wt % | magnesium content/wt % | halogen content/wt % |
| Example A1 | 50.9 | 0.3 | 65.6 | 2.0 | 18.5 | 7.4 | 6.5 |
| Example A2 | 50.7 | 0.51 | 69.07 | 2.37 | 14.61 | 6.2 | 7.75 |
| Example A3 | 51.0 | 0.45 | 64.7 | 1.52 | 17.63 | 8.73 | 7.42 |
| Example A4 | 50.6 | 1.43 | 72.5 | 1.46 | 10.8 | 6.7 | 8.54 |
| Example A5 | 50.8 | 0.75 | 62.3 | 1.25 | 19.35 | 9.4 | 7.7 |
| Example A6 | 50.4 | 1.5 | 61.2 | 0.8 | 15.4 | 9.4 | 13.2 |
| Starting carbon nanotube | — | 0.1 | 95.4 | 1 | 3.6 | — | — |
| o-CNT of Example A1 | — | 3.7 | 84.8 | 0.89 | 14.3 | — | — |
| Comparative Example A1 | 49.86 | 2.41 | 45.34 | | 21.51 | 32.62 | |

0.2-60 wt % of magnesium, 0.5-60 wt % of oxygen, and 0.1-40 wt % of chlorine, wherein the carbonaceous material has an x-ray photoelectron (XPS) spectrum in which the binding energy characteristic peak of the 2p electron of magnesium is located at >50.3 eV.

2. The carbonaceous material according to claim 1, comprising 10-90 wt % of carbon, 2-50 wt % of magnesium, 2-50 wt % of oxygen, and 1-30 wt % of chlorine.

3. The carbonaceous material according to claim 2, comprising 20-80 wt % of carbon, 5-30 wt % of magnesium, 5-40 wt % of oxygen, and 2-20 wt % of chlorine.

4. The carbonaceous material according to claim 3, comprising 25-41 wt % of carbon, 20-30 wt % of magnesium, 19-40 wt % of oxygen, and 4-20 wt % of chlorine.

5. The carbonaceous material according to claim 1, wherein, in the XPS spectrum of the carbonaceous material, a ratio of the content of chlorine as determined with a peak(s) in the range of 197.7-198.1 eV to the content of chlorine as determined with a peak(s) in the range of 199.7-200.1 eV is 0.5-2; a ratio of the content of oxygen as determined with a peak(s) in the range of 533.1-533.5 eV to a content of the oxygen element as determined with a peak(s) in the range of 531.8-532.2 eV is 0.2-5.

6. The carbonaceous material according to claim 1, wherein, as determined by an X-ray micro zone elemental analysis, a coefficient of variation for the content of magnesium obtained using XPS is 20% or lower.

7. The carbonaceous material according to claim 1, wherein said carbonaceous material has a peroxy group content of $\leq 2 \times 10^{-6}$ mol/g.

8. The carbonaceous material according to claim 1, wherein said carbonaceous material has a peroxy group content of $\leq 1 \times 10^{-6}$ mol/g.

9. The carbonaceous material according to claim 1, wherein said carbonaceous material has a peroxy group content of $\leq 0.8 \times 10^{-6}$ mol/g.

10. The carbonaceous material according to claim 1, wherein said carbonaceous material comprises at least one structural form selected from the group consisting of carbon nanotube, graphene, fullerene, nano-carbon particle, active carbon, thin-layer graphite, nano-carbon fiber, and nano-adamas.

11. A process for preparing a carbonaceous material of claim 1, wherein said process includes the following steps:
(1) Mixing a solid carbon source, a precursor and water to produce a mixture; wherein the precursor contains a magnesium source and a chlorine source, said magnesium source and said chlorine source are present in a dissolved state in the resulting mixture; the carbon element in said solid carbon source, and the magnesium element and the chlorine element in said precursor are present in a weight ratio of 1:(0.002-2):(0.01-20);
(2) Drying the resulting mixture obtained in Step (1) to produce a dried mixture;
(3) Calcining the dried mixture obtained in Step (2).

12. The process of claim 11, wherein the carbon element in said solid carbon source, and the magnesium element and the chlorine element in said precursor are present in a weight ratio of 1:(0.01-1):(0.1-10).

13. The process according to claim 11, wherein the weight ratio of water to the solid carbon source is (0.1-200):1.

14. The process of claim 11, wherein the calcination temperature is 200-500° C., and the calcination time is 0.5-48 hours.

15. The process of claim 14, wherein the calcination temperature is 300-450° C.

16. The process of claim 11, wherein the calcination is conducted in an oxygen-containing gas; and based on the total volume of the oxygen-containing gas, the oxygen-containing gas has an oxygen content of 2-25 vol %.

17. The process of claim 11, wherein said solid carbon source comprises at least one of carbon nanotube, graphene, fullerene, nano-carbon particle, thin-layer graphite, active carbon, nano-carbon fiber and nano-adamas; said magnesium source includes at least one of magnesium nitrate, magnesium nitrite, magnesium oxalate, magnesium oxide, magnesium hydroxide, magnesium sulfate, magnesium sulfite, magnesium tartrate, magnesium sulfide, magnesium cyanide, magnesium thiosulfate, magnesium rhodanate, magnesium iodide, magnesium chloride, magnesium bromide, magnesium acetate and magnesium carbonate; said chlorine source includes at least one of chlorine gas, magnesium chloride, hydrogen chloride, hypochlorous acid, magnesium hypochlorite, chloric acid, magnesium chlorite, perchloric acid and magnesium perchlorite.

18. The process of claim 11, wherein said precursor contains magnesium chloride and/or magnesium nitrate.

19. The carbonaceous material prepared with the process according to claim 11.

20. A method for catalytic oxidation of hydrocarbons, comprising: oxidizing a hydrocarbon stream in the presence of the carbonaceous material of claim 1.

21. The method according to claim 20, wherein said hydrocarbon has a carbon atom number of 2-15, said hydrocarbon comprises at least one of an alkane, an alkene and an aromatic hydrocarbon containing alkyl group(s); said alkyl contains at least two carbon atoms.

22. The method according to claim 20, wherein said hydrocarbon comprises at least one of butane, 1-butene, ethylbenzene, propane, ethane and pentane.

\* \* \* \* \*